United States Patent [19]

Rudolph et al.

[11] 3,931,355

[45] Jan. 6, 1976

[54] RADICAL-INITIATED POLYMERIZATION REACTIONS AND MIXTURE

[75] Inventors: Hans Rudolph, Krefeld-Bockum; Hans-Joachim Traenckner, Krefeld-Fischelin, both of Germany

[73] Assignee: Bayer Aktiengesellschaft, Germany

[22] Filed: Jan. 24, 1974

[21] Appl. No.: 436,181

Related U.S. Application Data

[63] Continuation-in-part of Ser. No. 315,329, Dec. 15, 1972, abandoned.

[30] Foreign Application Priority Data

Dec. 24, 1971 Germany............................ 2164482

[52] U.S. Cl.......... 260/865; 252/431 R; 260/47 UA; 260/63 K; 260/80 C; 260/88.3 R; 260/88.3 L; 260/89.1; 260/89.3; 260/89.7; 260/91.7; 260/92.8 R; 260/93.5 R; 260/94.2; 260/94.9 CD; 260/448.8 A

[51] Int. Cl.²............................................. C08F 4/16
[58] Field of Search... 260/865, 63 K, 47 UA, 80 C, 260/88.3 R, 88.3 L, 89.1, 89.3, 94.2 R, 94.9 CD, 93.5 R, 91.7, 89.7 R, 92.8 R

[56] References Cited
UNITED STATES PATENTS

| 3,313,863 | 4/1967 | Schnell et al. ...................... 260/864 |
| 3,313,864 | 4/1967 | Rudolph et al. ..................... 260/864 |
| 3,531,438 | 9/1970 | Schnell et al. ........................ 260/75 |

*Primary Examiner*—Donald E. Czaja
*Assistant Examiner*—E. A. Nielsen
*Attorney, Agent, or Firm*—Connolly and Hutz

[57] ABSTRACT

A method of initiating polymerization reactions by the silyl-ethers of the tetraaryl-1.2-glycols.

18 Claims, No Drawings

RADICAL-INITIATED POLYMERIZATION REACTIONS AND MIXTURE

This application is a continuation-in-part of our application Ser. No. 315,329, filed Dec. 15, 1972, now abandoned.

This invention relates to free radical polymerization.

The invention especially relates to the use of silyl-ethers of the tetraaryl-1,2-glycols as initiators for polymerization reactions which are to be initiated by radicals.

It is known from German Auslegeschrift (German Published Specification) 1,216,877 and German Pat. Specification 1,219,224 to use as polymerization catalysts tetraaryl-glycols of which the hydroxyl groups can be etherified.

Substances polymerizable by radicals and containing these catalysts are distinguished by the fact that they can be stored for a practically unlimited period at room temperature and by the fact that the course of their curing can be controlled easily and reliably by controlling the temperature. A further advantage of these catalysts is that in contrast to the known peroxide catalysts their handling presents no hazard whatsoever.

A disadvantage of these catalysts is their relatively low reactivity. Thus, complete curing is not achievable within a reasonable time at below 80°C and is only achievable at temperatures of between 80° and 140°C if relatively high concentrations (equal to or greater than 2%) of the catalysts are employed. Even then, however, many hours are still required for complete curing of the moldings. This is a major disadvantage since the moving belt technique, which at the present time is customary in the plastics industry, demands rapid curing times.

Furthermore, the use of catalysts in high concentrations must be rejected not only for economic reasons; they frequently noticeably impair the properties of the cured products.

It has now been found that silyl-ethers of the tetraaryl-1,2-glycols are more reactive than the above mentioned compounds by a factor of about 50.

Accordingly, one subject of the present invention is a method of starting radical-initiated polymerization reactions by the use of silyl-ethers of the tetraaryl-1,2-glycols. The invention also provides polymerizable substances or mixtures of substances which contain the above mentioned silyl-ethers.

Suitable silyl-ethers of the tetraaryl-1,2-glycols are compounds of the general formula

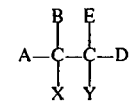

in which

A, B, D and E denote substituted or unsubstituted phenyl or unsubstituted 2-naphthyl radicals, and X and Y denote trialkyl- or triaryl-siloxy radicals.

The phenyl radicals A, B, D and E may have between 6 and 18 carbon atoms and may be substituted in 2-, 3-, 4-, 5- and/or 6-position by alkyl or alkoxy radicals with up to 4 carbon atoms, by chlorine or bromine or in 3-, 4- and/or 5-position by phenyl radicals; moreover A and B respectively D and E may form together with the corresponding carbon atom of the general formula the fluorenyliden radical; the alkyl radicals of the siloxy radicals are e.g. $C_1$-$C_4$-alkyl radicals like methyl, ethyl, propyl, butyl, isopropyl, sec.-butyl, isobutyl or tert.-butyl; the aryl radicals of the siloxy radicals are e.g. unsubstituted phenyl radicals or methyl- or methoxy-substituted phenyl radicals, such as toluyl or methoxyphenyl radicals. It is understood, of course, that a di-fluorenyl is a special tetra-aryl ethane.

The silyl compounds to be employed according to the invention are effective above 50°C; even at relatively low temperatures e.g. below 100°C, 0.05 to 0.2% by weight of these compounds, based on the weight of the polymerizable substance, suffices completely to cure the substance to be polymerized, or the mixture of substances to be polymerized, in a short time.

The silyl-ether compounds can be manufactured in a simple known manner by reacting benzophenone or its appropriate derivatives, in tetrahydrofurane, with magnesium and, for example, trimethylchlorosilane, in the presence of hexamethylphosphoric acid triamide.

The following compounds may be mentioned as examples:

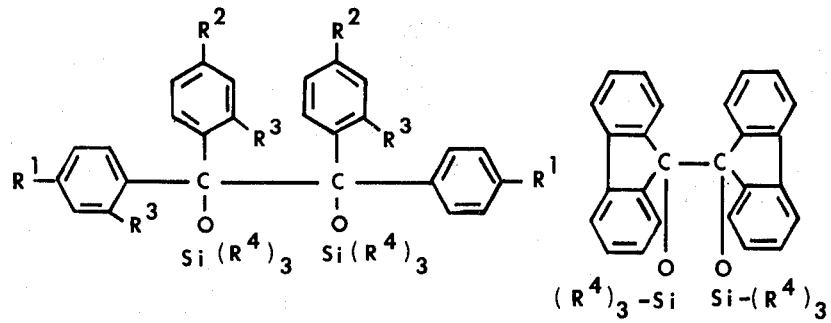

| $R^1$ | $R^2$ | $R^3$ | $R^4$ | Melting point (°C) |
|---|---|---|---|---|
| H | H | H | —$CH_3$ | 112 |
| $CH_3$ | H | H | —$CH_3$ | 86 |
| $CH_3$ | $CH_3$ | H | —$CH_3$ | 106 |
| $CH_3$ | $CH_3$ | $CH_3$ | —$CH_3$ | liquid |
| $C_2H_5$ | H | H | —$CH_3$ | 76 |
| $C_2H_5$ | $C_2H_5$ | H | —$CH_3$ | 103 |
| O—$CH_3$ | H | H | —$CH_3$ | liquid |
| Cl | H | H | —$CH_3$ | 117 |

The radical formation is initiated by heating the compounds in polymerizable systems to above 50°C. The curing can then take place in one step but can, if desired, also take place in several steps by suitably controlling the temperature. (Compare British Patent Specification 1,041,614.)

Polymerizable substances, the curing of which may be performed according to the invention, include practically all compounds which contain one or more polymerizable double bonds in the molecule, for example mono- and conjugated diolefins such as ethylene, propylene, butadiene, isoprene, chloroprene; vinyl-substituted benzenes and derivatives thereof, such as styrene, α-methylstyrene, halogenated styrenes, divinyl benzene, vinyltoluene, N-vinyl heterocycles such as N-vinyl pyrrolidone, N-vinyl carbazol, vinyl pyridine; α,β-olefinically unsaturated carboxylic acids and their derivatives, such as acrylic and methacrylic acid or esters or amides, such as methacrylic acid methyl ester, ethylene glycol bis-methacrylate, (meth) acrylic acid esters of epoxy resins, acrylonitrile, methacrylonitrile; vinyl esters such as vinyl acetate, vinyl benzoate, adipic acid divinyl ester; vinyl ketones such as vinylmethylketone, isopropenylmethylketone; vinyl or vinylidene halides such as vinyl and vinylidene chloride; allyl esters such as allyl acetate, diallyl phthalate, allyl acrylate, triallyl cyanurate, triallyl phosphate, diallyl isophthalate; diallyl carbonate; di(allylphenyl) carbonates; di(vinylphenyl) carbonates; polyol polyacrylates and -methacrylates; N.N'-methylene-bis-acrylamide and -methacrylamide; the silyl ethers according to the invention are not only suitable for homopolymerization reactions, but also for the copolymerization including e.g. the common polymerization of ethylene and carbon monoxide or of ethylene and maleic acid dimethylester as well as for the telomerization, e.g. between ethylene and acetic aldehyde, between ethylene and benzaldehyde, including the 1:1-addition of the formed radicals to unsaturated compounds such as maleic acid esters.

Molding and coating compositions of unsaturated polyesters and copolymerizable monomers are particularly susceptible to curing according to the invention.

By unsaturated polyesters there are understood the customary condensation products of dihydric alcohols and α,β-unsaturated dicarboxylic acids containing, if appropriate, a radical with an allyl ether structure which condensation products optionally contain further mono-, di- or poly-functional alcohols or carboxylic acids, which can be free of olefinic double bonds.

Suitable copolymerizable monomeric compounds are also the unsaturated compounds customary in polyester technology, which possess vinyl groups optionally substituted in the α-position or allyl groups optionally substituted in the β-position, such as, for example, styrene, vinyltoluene, divinylbenzene, vinyl acetate, acrylic acid and its esters, acrylonitrile, methacrylic acid and its corresponding derivatives as well as allyl esters, such as allyl acetate, allyl acrylate, phthalic acid diallyl ester, triallyl phosphate and triallyl cyanurate.

It is possible to use a simple color reaction for testing the temperature at which the beginning dissociation of the particular catalyst becomes noticeable, and hence its optimum working range. This is because the radicals produced during the thermal decomposition possess the capacity of disolorising quinonoid dyestuffs, so that the start of radical formation can be determined. To carry out this text, the quinonoid dyestuff is dissolved in an oxygen-free solvent, such as glycol or xylene, and a small amount of the compound is added. The discoloration temperature is the temperature at which a noticeable dissociation commences.

In the Examples which follow the parts and percentages mentioned are parts and percentages by weight, unless otherwise stated.

Example 1

An unsaturated polyester resin, manufactured from 72 parts of o-phthalic anhydride, 98 parts of maleic anhydride and 114 parts of 1,2-propylene glycol at 200°C, was dissolved in styrene to give a 66% strength solution and stabilized with 0.01 part of hydroquinone. 0.05 part of tetra-(4-tolyl)-1,2-bis-(trimethylisiloxy)-ethane was added and the mixture was heated to 60°C in as short a time as possible. After this temperature had been reached, the resin was gelled in 3 minutes and 30 seconds. It was completely cured after about 6 minutes.

Example 2

An unsaturated polyester resin, as described in Example 1, was treated with 0.05% of diphenyl-di-(4-tolyl)-1,2-bis-(trimethylsiloxy)-ethane. It was again heated to 60°C as rapidly as possible, whereupon the resin started to gel after 3 minutes and 15 seconds and had cured completely after 5 minutes.

Example 3 (for comparison)

Example 1 was repeated, but instead of 0.05 part of tetra-(4-tolyl)-1,2-bis-(trimethylsiloxy)-ethane, 0.05 part of tetraphenyl-ethylene glycol was incorporated. On warming to 60° and up to 120°C inclusive, no polymerization was observable. Only on addition of 0.5 part of the initiator was polymerization observed at 100°C, but this did not give a fully cured product in 60 minutes.

Example 4 (for comparison)

A polyester moulding composition manufactured according to Example 1 was mixed with 0.05 part of tetraphenylethylene glycol dimethyl ether. On warming to 60°C, no gelling occured. Only on addition of more than 0.8 part of the initiator was gelling observable.

Example 5

An oxygen-free solution of the methylene blue in glycol was warmed, with addition of the compound, shown in the following table, to be tested. The solution in each case underwent discoloration at the temperature indicated.

| Substance | Discoloration temperature (°C) |
|---|---|
| Benzpinacol | 135 |
| Tetraphenyl-1,2-bis-(trimethylsiloxy)-ethane | 70 |
| Tetra-4-tolyl-1,2-bis-(trimethylsiloxy)-ethane | 65 |
| Bis-(4-tolyl)-bisphenyl-1,2-bis-(trimethylsiloxy)-ethane | 65 |

Example 6

100 g of methyl methacrylate, which was shaken with dilute sodium hydroxide solution and distilled under reduced pressure in order to obtain it inhibitor-free, was treated with 0.05% of bis-fluorenyl-1,2-bis-(trimethylsiloxy)-ethane and heated to refluxing. After 15 minutes, the viscosity began to rise markedly. The solution subsequently gelled. The reaction mixture was heated under reflux for 1 hour, the polymer was dissolved in dichloromethane and precipitated by adding a portion of methanol.

Example 7 (for comparison)

Example 6 was repeated, but instead of 0.05% of bis-fluorenyl-1.2-bis-(trimethylsiloxy)-ethane 0.05% of benzpinacol were employed. After 8 hours, no gelling had occured.

What we claim is:

1. A method of polymerizing a substance containing polymerizable carbon-carbon double bonds which comprises polymerizing the substance in the presence of a trialkyl or triaryl silyl-ether of a tetraaryl-1,2-glycol.

2. A method as claimed in claim 1 wherein the silyl-ether is of the formula

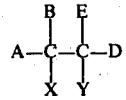

in which A, B, D and E are each a member selected from the group consisting of an unsubstituted 2-naphthyl radical, an unsubstituted phenyl radical, a phenyl radical substituted in at least one of the 2-, 3-, 4-, 5- and 6-positions by chlorine or bromine, a phenyl radical having 6–18 carbon atoms substituted in at least one of the 2-, 3-, 4-, 5- and 6-positions by alkyl having up to 4 carbon atoms, a phenyl radical having 6–18 carbon atoms substituted in at least one of the 2-, 3-, 4-, 5- and 6-positions by alkoxy having up to 4 carbon atoms, a phenyl radical with 12 to 18 carbon atoms substituted in at least one of the 3-, 4- and 5-positions by phenyl, in which A and B and D and E may form together with the carbon atom to which they are attached the fluorenylidene radical, and in which X and Y are trialkyl-siloxy or triaryl-siloxy radicals.

3. A method as claimed in claim 2 wherein the silylether is of the formula

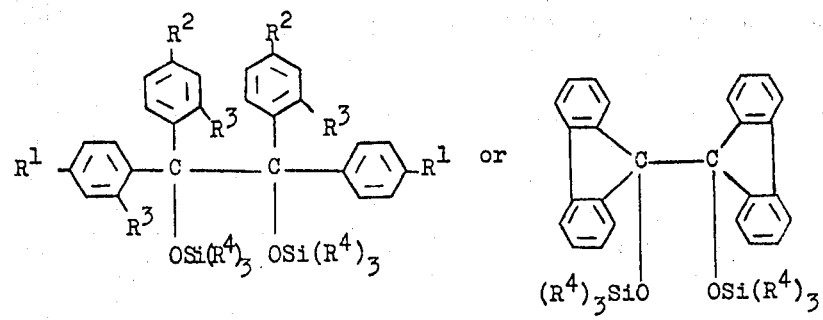

in which $R^1$ is hydrogen, methyl, ethyl or methoxy; $R^2$ is hydrogen, methyl or ethyl; $R^3$ is hydrogen or methyl and $R^4$ is methyl.

4. A method as claimed in claim 1 wherein the polymerization is conducted at a temperature above 50°C.

5. A method as claimed in claim 1 wherein the silyl-ether is present in an amount of 0.05 to 0.2% by weight, based on the weight of the polymerizable substance.

6. A method as claimed in claim 1 wherein the polymerizable substance is a member selected from the group consisting of a monoolefin, a conjugated diolefin, a vinyl-substituted benzene or a derivative thereof, a N-vinyl heterocycle, an α,β-olefinically unsaturated carboxylic acid or an ester, amide or nitrile thereof, a vinyl ester, a vinyl ketone, an allyl ester, a di(allylphenyl) carbonate, a vinyl halide, a vinylidene halide, a di(vinylphenyl) carbonate, a polyol acrylate, a polyol methacrylate, a N,N'-methylene-bis-acrylamide and a N,N'-methylene-bis-methylacrylamide.

7. A method as claimed in claim 1 wherein the polymerizable substance is a mixture of an unsaturated polyester of a dihydric alcohol and an α,β-unsaturated dicarboxylic acid and a copolymerizable ethylenically unsaturated monomer.

8. A method as claimed in claim 7 wherein the silyl-ether is tetra-(4-tolyl)-1,2-bis-(trimethylsiloxy)-ethane.

9. A method as claimed in claim 1 wherein the polymerizable substance is methyl methacrylate and the silyl-ether is bis-fluorenyl-1,2-bis-(trimethylsiloxy)-ethane.

10. A polymerizable mixture comprising a substance containing polymerizable carbon-carbon bonds and a silyl-ether of a tetraaryl-1,2-glycol.

11. A mixture as claimed in claim 10 wherein the silyl-ether is of the formula

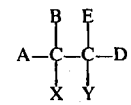

in which A, B, D and E are each a member selected from the group consisting of an unsubstituted 2-naphthyl radical, an unsubstituted phenyl radical, a phenyl radical substituted in at least one of the 2-, 3-, 4-, 5- and 6-positions by chlorine or bromine, a phenyl radical having 6–18 carbon atoms substituted in at least one of the 2-, 3-, 4-, 5- and 6-positions by alkyl having up to 4 carbon atoms, a phenyl radical having 6–18 carbon atoms substituted in at least one of the 2-, 3-, 4-, 5- and 6-positions by alkoxy having up to 4 carbon atoms, a phenyl radical with 12 to 18 carbon atoms substituted in at least one of the 3-, 4- and 5-positions by phenyl, in which A and B and D and E may form together with the carbon atom to which they are attached the fluorenylidene radical, and in which X and Y are trialkyl-siloxy or triaryl-siloxy radicals.

12. A mixture as claimed in claim 11 wherein the silyl-ether is of the formula

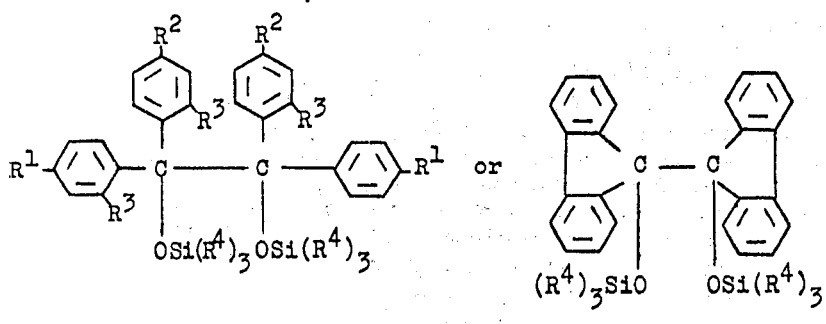

in which $R^1$ is hydrogen, methyl, ethyl or methoxy; $R^2$ is hydrogen, methyl or ethyl; $R^3$ is hydrogen or methyl and $R^4$ is methyl.

13. A mixture as claimed in claim 11 wherein the silyl-ether is present in an amount of 0.05 to 0.08% by weight, based on the weight of the polymerizable substance.

14. A mixture as claimed in claim 11 wherein the polymerizable substance is a member selected from the group consisting of a mono-olefin, a conjugated diolefin, a vinyl-substituted benzene or a derivative thereof, a N-vinyl heterocycle, an α,β-olefinically unsaturated carboxylic acid or an ester, amide or nitrile thereof, a vinyl ester, a vinyl ketone, an allyl ester, a di(allylphenyl) carbonate, a vinyl halide, a vinylidene halide, a di(vinylphenyl) carbonate, a polyolacrylate, a polyol methacrylate, a N,N'-methylene-bis-acrylamide and a N,N'-methylene-bis-methacrylamide.

15. A mixture as claimed in claim 11 wherein the polymerizable substance is a mixture of an unsaturated polyester of a dihydric alcohol and α,β-unsaturated dicarboxylic acid and a copolymerizable ethylenically unsaturated monomer.

16. A mixture as claimed in claim 15 wherein the silyl-ether is tetra-(4-tolyl)-1,2-bis-(trimethylsiloxy)-ethane or diphenyl-di-(4-tolyl)-1,2-bis-(trimethylsiloxy)-ethane.

17. A mixture as claimed in claim 15 in the form of a molding or coating composition.

18. A mixture as claimed in claim 10 comprising methyl methacrylate and bis-fluorenyl-1,2-bis-(trimethylsiloxy)-ethane.

* * * * *